United States Patent [19]

Schlenoff et al.

[11] Patent Number: 5,258,478
[45] Date of Patent: Nov. 2, 1993

[54] LOW SELF-ABSORBING, INTRINSICALLY SCINTILLATING POLYMERS

[75] Inventors: Joseph B. Schlenoff; Jayesh Dharia; Kurtis F. Johnson, all of Tallahassee, Fla.

[73] Assignee: Florida State University, Tallahassee, Fla.

[21] Appl. No.: 874,748

[22] Filed: Apr. 27, 1992

[51] Int. Cl.$^5$ ............... C08F 216/36; C08F 220/14; C08F 212/08; C08F 220/42
[52] U.S. Cl. ................................ 526/316; 526/293; 526/297; 526/312; 526/328.5; 526/334; 526/347
[58] Field of Search ........................................ 526/316

[56] References Cited

U.S. PATENT DOCUMENTS

| | | | |
|---|---|---|---|
| 3,985,566 | 10/1976 | Buhr et al. | 96/115 R |
| 4,011,266 | 3/1977 | Pearson et al. | 260/590 FB |
| 4,452,720 | 6/1984 | Harada et al. | 252/301 |
| 4,591,600 | 5/1986 | Creuzet et al. | 514/456 |
| 4,758,679 | 7/1988 | Schmitthenner | 549/403 |
| 5,100,587 | 3/1992 | Clough et al. | 252/646 |
| 5,110,500 | 5/1992 | Walker | 252/301.16 |

OTHER PUBLICATIONS

Qualitz et al., "Pressure-sensitive recording material with improved stability, fading resistance and heat resistance", Chem. Abstr. 96: 208445p (1982) p. 608.
Zorn et al., "Pilot study of new radiation-resistant plastic scintillators doped with 3-hydroxyflavone", Chem. Abstr. 110: 30241m (1989) p. 422.

Primary Examiner—Joseph L. Schofer
Assistant Examiner—Wu C. Cheng
Attorney, Agent, or Firm—Senniger, Powers, Leavitt & Roedel

[57] ABSTRACT

Polymers containing covalently-bonded, low self-absorbing, scintillating chromophores, polymerizable chromophores of the formula:

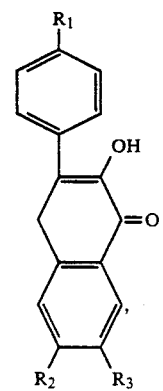

wherein $R_1$ is vinyl, α-methyl vinyl, vinyl phenyl, or vinyl benzyl, and $R_2$ and $R_3$ are independently hydrogen, alkyl, aryl, cyano, nitro, halo, or ether, and a process for the preparation of polymers containing low self-absorbing, scintillating chromophores.

11 Claims, No Drawings

LOW SELF-ABSORBING, INTRINSICALLY SCINTILLATING POLYMERS

BACKGROUND OF THE INVENTION

This invention relates to plastics (polymers) useful as fluorescent materials. More specifically, it relates to low self-absorbing, intrinsically scintillating polymers particularly useful as scintillating detectors for high-energy radiation and particles. The polymers comprise chromophores chemically bound to vinyl segments.

The detection of high-energy radiation can be accomplished through the use of compounds which scintillate (emit light) when a particle of radiation impinges on, or passes near, such compounds. Organic molecules capable of light emission based on fluorescence are called fluors, or chromophores. In the process of fluorescence, a chromophore is excited by absorbing an energy source, such as a photon, and then emits a photon of lower energy (longer wavelength) upon relaxation. Excitation of chromophores can also be produced by radiationless transfer of energy or by other high energy processes. Thus, the ability of chromophores to scintillate in this manner makes them a useful material for the detection or tracking of ionizing particles.

In current technological applications, chromophores are typically dispersed in a plastic medium, such as polystyrene. The term "scintillator" is applied to the polymer/chromophore ensemble.

A particularly useful chromophore is 3-hydroxyflavone (3HF). 3HF has the formula:

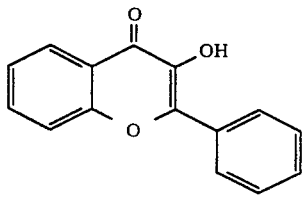

3HF is the chromophore of choice for many commercial scintillators because it emits a significantly longer wavelength than it absorbs. On excitation, a proton is transferred to the carbonyl group of the 3HF molecule in the following manner:

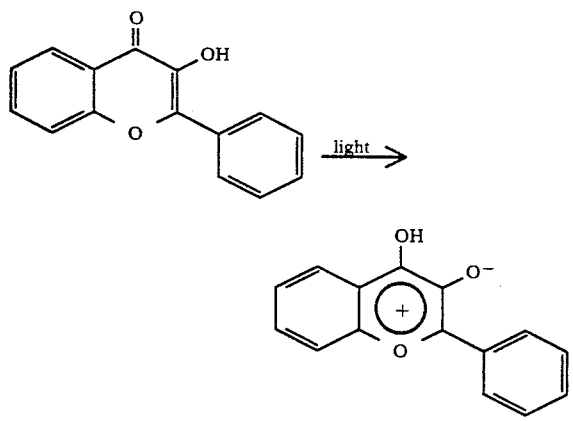

This property, known as proton-transfer fluorescence, produces a greater Stokes shift (the difference in absorbed and emitted wavelengths) for the 3HF molecule than occurs in other chromophore molecules. This enhanced Stokes shift is commercially significant in several respects. First, it bypasses radiation-induced color centers in the plastic medium which attenuate the light output of the scintillator and shorten its useful life. Second, 3HF's greater Stokes shift makes it a low self-absorbing fluor, since photons emitted at greatly reduced wavelengths are much less likely to be reabsorbed by another chromophore before exiting the scintillator.

While scintillators utilizing 3HF molecules dissolved in a plastic matrix are preferable to alternative scintillating materials for the reasons discussed above, they are not without shortcomings. For instance, there is a limit to the solubility of 3HF in plastics. Typically, scintillators using 3HF chromophores are limited to a chromophore concentration of about 1.2% (by weight at room temperature). This restricts the maximum level of brightness to which 3HF scintillators are capable. Further, over time, scintillators using chromophore molecules dispersed in a plastic medium are subject to chromophore migration and phase separation. This phenomenon adversely affects the quality of the scintillation produced by the material and reduces the useful life of the scintillator.

SUMMARY OF THE INVENTION

Among the objects of the invention, therefore, may be noted the provision of low self-absorbing, intrinsically scintillating polymers in which the chromophores are chemically bound to the plastic medium in which they are dispersed; the provision of scintillators with limitless chromophore solubility; the provision of scintillators with improved brightness, and the provision of scintillators which are not subject to chromophore migration or phase separation; the provision of novel chromophores which are readily polymerizable; and the provision of a process for the preparation of such intrinsically scintillating polymers.

Briefly, therefore, the present invention is directed to a polymerizable chromophore of the formula:

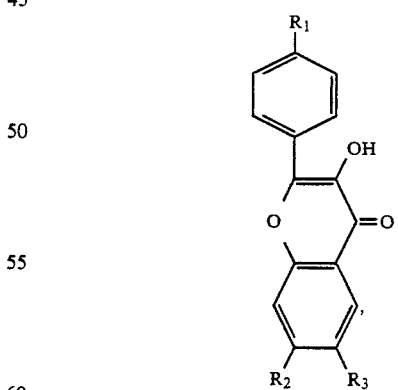

wherein $R_1$ is vinyl, -methyl vinyl, vinyl phenyl, or vinyl benzyl, and $R_2$ and $R_3$ are independently hydrogen, alkyl, aryl, cyano, nitro, halo, or an ether group.

The present invention is further directed to an intrinsically scintillating polymer having a repeating unit in the polymer chain derived from a chromophore of the formula:

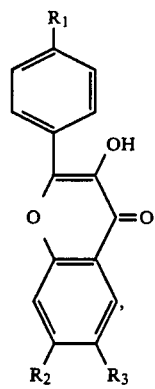

wherein $R_1$ is vinyl, α-methyl vinyl, vinyl phenyl, or vinyl benzyl, and $R_2$ and $R_3$ are independently hydrogen, alkyl, aryl, cyano, nitro, halo, or an ether group.

The present invention is also directed to a process for the preparation of an intrinsically scintillating polymer having a repeating unit in the polymer chain derived from a chromophore of the formula:

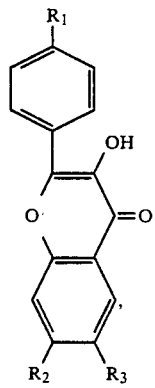

wherein $R_1$ is vinyl, α-methyl vinyl, vinyl phenyl, or vinyl benzyl, and $R_2$ and $R_3$ are independently hydrogen, alkyl, aryl, cyano, nitro, halo, or ether comprising contacting a vinyl aldehyde with 2-hydroxyacetophenone to produce a vinyl hydroxyflavone monomer and polymerizing the monomer using a radical initiator.

Other objects and features will be in part apparent and in part pointed out hereinafter.

DESCRIPTION OF THE PREFERRED EMBODIMENT

In accordance with the present invention it has been discovered that, by utilizing the synthetic route disclosed by the present invention, chromophores including the 3HF structure may be covalently bonded to moieties incorporating a vinyl group, thereby producing a polymerizable chromophore. These novel chromophores may be used to produce low self-absorbing, intrinsically scintillating polymers which can be used as scintillators having limitless chromophore solubility, brighter fluorescence, and which are not subject to chromophore migration and phase separation. These novel scintillating polymers will also undergo copolymerization reactions with other plastic materials, such as polystyrene.

The present invention is directed to a polymerizable chromophore 1 and its derivatives, the structure of which is depicted below.

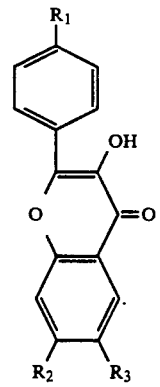

As discussed above, $R_1$ is vinyl, α-methyl vinyl, vinyl phenyl, or vinyl benzyl, and $R_2$ and $R_3$ are independently hydrogen, alkyl, aryl, cyano, nitro, halo, or ether.

The structure of a preferred chromophore, in which $R_1$ is vinyl and $R_2$ and $R_3$ are both hydrogen is shown below:

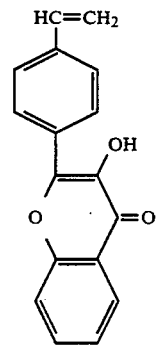

According to IUPAC rules, the name of chromophore 2 is 4-vinyl, 3-hydroxyflavone.

Polymerizable vinyl 3-hydroxyflavones (vinyl 3HFs) may be produced by contacting a vinyl aldehyde with a 2-hydroxyacetophenone under certain prescribed conditions. The general formula for the synthesis of a vinyl 3HF from a vinyl aldehyde and 2-hydroxyacetophenone is depicted as follows:

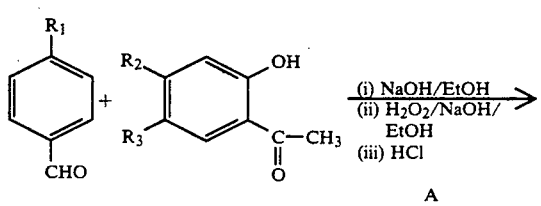

-continued

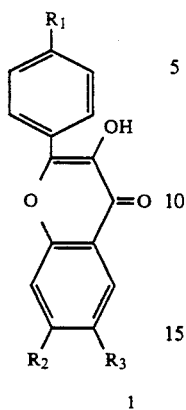

The substituents $R_1$, $R_2$ and $R_3$ are as defined above.

In a particularly preferred procedure, 4-vinyl benzaldehyde is prepared from 4-chlorostyrene and combined with 2-hydroxyacetophenone in an ethyl alcohol solution to which NaOH is added. After allowing the reaction mixture to sit at room temperature overnight, a solution of hydrogen peroxide in aqueous ethyl alcohol is added and the reaction mixture is acidified to complete the preparation of 4-vinyl 3-hydroxyflavone.

Alternatively, a vinyl phenyl hydroxyflavone may be prepared by synthesizing 4-styrene trimethyltin and combining it with 4-bromobenzaldehyde to produce 4'-vinyl, 4-biphenyl aldehyde. This intermediate compound is then reacted with 2-hydroxyacetophenone to produce the vinyl phenyl hydroxyflavone. This reaction scheme proceeds as follows:

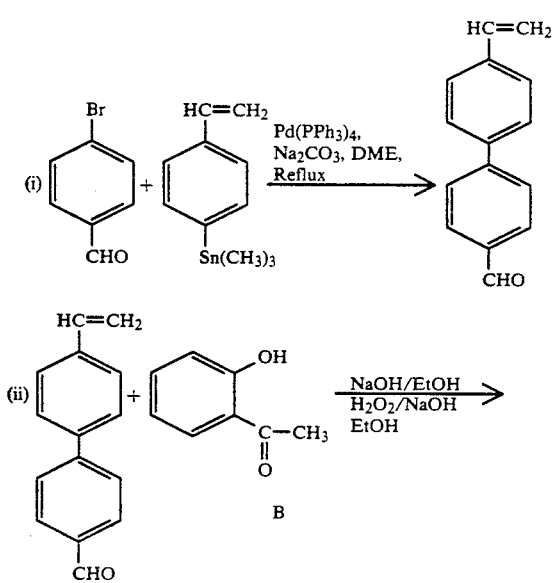

-continued

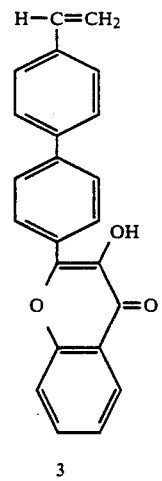

A third approach to the preparation of polymerizable chromophores of the type described herein is exemplified by the preparation of vinyl 3HF using a synthetic route which calls for the preparation of 4'vinyl, 4-aldehyde diphenylmethane by combining 4-trimethyltin styrene with bromomethylbenzaldehyde. The 4'-vinyl, 4-aldehyde diphenylmethane may then be combined with 2-hydroxyacetophenone as described above for conversion to vinyl benzene 3HF. This reaction scheme is set forth as follows:

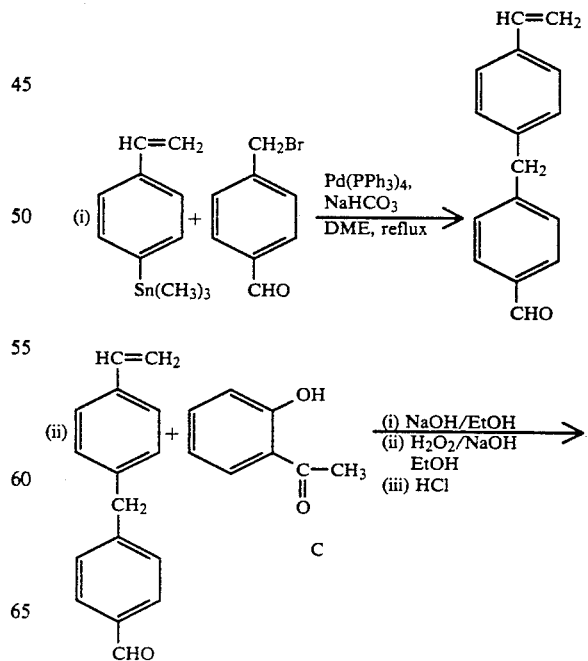

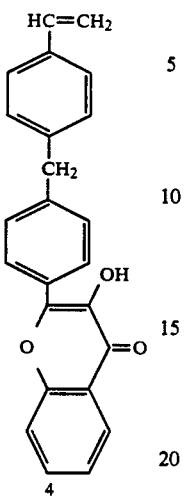

4

The hydrogens at the $R_2$ and $R_3$ positions of chromophore 1, as well as hydrogens attached to the vinylic carbons at $R_1$ may be replaced by a number of substituents without significantly affecting the ability of the vinyl 3HFs of this invention to function effectively as polymerizable chromophores. Among the functional groups which may readily replace the hydrogens at these positions are alkyl, aryl, cyano, nitro, halo, or ether. Alkyl groups are preferably $C_{1-10}$ alkyl, and most preferably, methyl or ethyl. Aryl groups are preferably $C_{6-15}$ aryl, and most preferably, phenyl. Exemplary compounds within the generic formula are depicted hereinbelow:

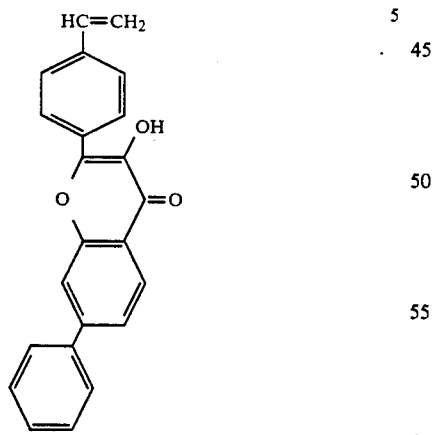

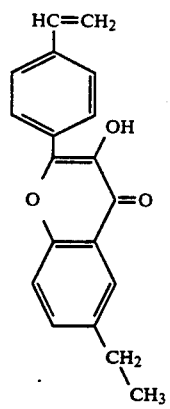

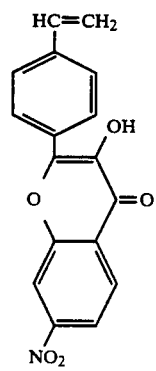

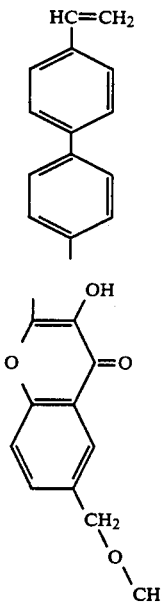

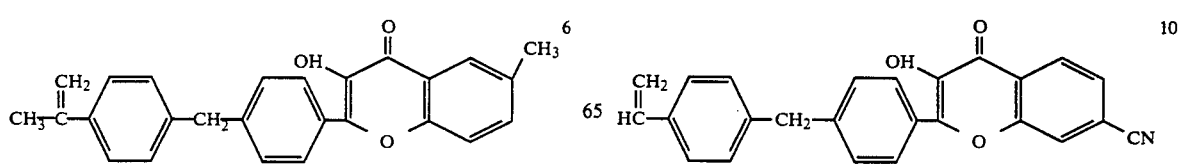

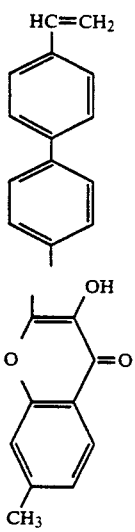

11

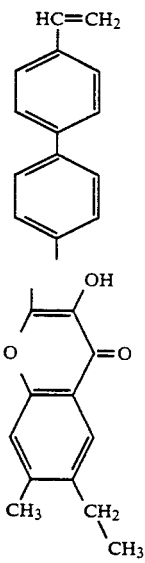

12

13

In accordance with the process of the present invention, a poly(vinyl)-3HF is prepared which may be utilized as a scintillator. In this process, vinyl 3HF monomer (chromophore 1) is prepared by contacting 2-hydroxyacetophenone with a vinyl aldehyde, for example, using one of the reaction schemes discussed above. The vinyl 3HF monomer thus produced is then polymerized using a radical initiator such as azobisisobutyronitrile (AIBN). A representative example of the above-described polymerization reaction is depicted as follows:

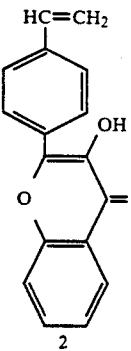
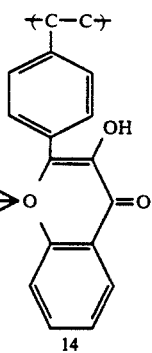

2  D  14

Co-polymers consisting of repeating units derived from vinyl 3HF and at least one other polymerizable monomer may also be Produced according to the method of this invention. Copolymers using different weight percentages of vinyl 3HF may be prepared using a radical initiator as discussed above. The vinyl 3HF monomer is combined with another monomer, such as styrene, in a desired ratio of the monomers. An example of a copolymer produced by the copolymerization reaction of vinyl 3HF and styrene is set forth below:

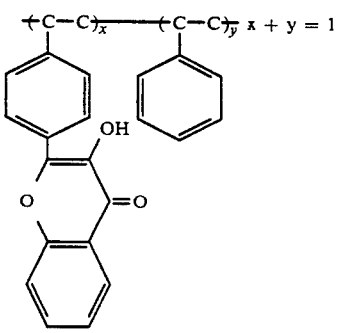

15

The same procedure may be utilized to create a copolymer of vinyl 3HF with other repeating units in the polymer chain. For example, vinyl 3HF monomer may be combined with either vinyl toluene or methyl methacrylate monomer in selected proportions to produce copolymers having a predetermined ratio of vinyl 3HF to the other monomer.

The vinyl 3HF polymers and copolymers of this invention produce films which may be used as scintillators. For example, these scintillating polymers may be used to detect ionizing radiation emanating from particle accelerators. Preferably, for use as scintillators the chromophore concentration of the polymer is between about 0.5% and about 10% (by weight), and most preferably, about 5%.

A polymer comprising 5% by weight vinyl 3HF will scintillate with substantially greater brightness than 3HF dissolved in a plastic medium, which has a maximum solubility of about 1.2%. Additionally, chromophore migration and phase separation between the chromophores and the plastic are prevented since the chromophore units are covalently bonded to the polymer. Further, the high concentration of chromophores ameliorates the loss in light output due to irradiation damage.

The following examples illustrate the invention:

EXAMPLE 1

Preparation of 4'-Vinyl 3-Hydroxy Flavone (4'V3HF)

a) 4-vinyl benzaldehyde. 4-chlorostyrene (Fluka) was dried over $CaH_2$ prior to use. Anhydrous dimethyl formamide (DMF)(Aldrich) was used as received. THF was dried over sodium benzophenone complex and was distilled prior to use. All glassware used was flame dried and cooled under dry nitrogen prior to use. Nitrogen was passed through a column of silica blue and drient. A standard cannular transfer technique was used to transfer air sensitive reagents.

7.6 gms (0.312 moles) of Mg tunings were transferred to an RB flask containing 50 ml of dry THF under nitrogen atmosphere. 2 ml of ethyl bromide was then added to the Mg metal and the reaction mixture was warmed to 50°-55° C. The mixture reacted vigorously and activated Mg metal was formed. A solution of 20 ml (0.156 moles) of 4-chlorostyrene in 50 ml of THF was added dropwise at room temperature to the activated Mg. The reaction mixture was stirred for an additional two hours. A dark gray solution appeared and was allowed to settle down. In a separate IL RB flask, a solution of 12 ml (0.15 moles) of anhydrous DMF was prepared in 300 ml of THF. The DMF solution was cooled in an icebath under dry nitrogen atmosphere for 15 mins. Grignard reagent was added dropwise to the DMF solution over a period of 1 hr with vigorous stirring. The reaction flask was then allowed to stir for three hrs. at 5° C. and RT overnight. The reaction was quenched by pouring the entire reaction mixture into 300 ml of dilute HCl in an icebath. The product was separated by solvent extraction with ether. The ether layer was dried over anhyd. $MgSO_4$ and filtered. Finally, ether was evaporated under reduced pressure. A viscous yellow liquid was obtained and was dried under vacuum for 2 hrs and stored in a freezer at $-10°$ C. containing a small amount of hydroquinone as an inhibitor. A yield of 65% high purity (above 95%) 4-vinyl benzaldehyde was obtained.

b) 4'-vinyl-3-hydroxyflavone. 2-hydroxyacetophenone (Aldrich) was used as received. Ethyl alcohol was distilled prior to use. 4-vinyl benzaldehyde was synthesized using the procedure described in Example 1(a).

13 gms of 4-vinyl benzaldehyde 0.955 moles) was added to a flask containing 13.9 gms of 2-hydroxyacetophenone (0.955) in 150 ml alcohol. In a separate RB flask, 13 gms of NaOH was dissolved in 100 ml of aqueous ethyl alcohol (75%). The NaOH solution was added to the reaction mixture at once. The color of the solution immediately changed from colorless to yellow to pink, and then, finally, to a dark red precipitate. The solution was allowed to sit at room temperature overnight. The next morning, 6 gms of NaOH in 200 ml of aqueous ethyl alcohol (75%) was added to the Precipitate and the reaction mixture was cooled in an icebath for 15 mins. In a separate RB flask, a solution of 50 ml of 30% hydrogen peroxide solution in 50 ml of aqueous ethyl alcohol (75%) was added to the reaction flask at once at 0°-5° C. The red colored precipitate dissolved immediately and the color of the solution slowly changed from red to yellow. The solution was gradually warmed to room temperature and was stirred for 6 hrs. The reaction mixture was neutralized with dil. HCl at 0°-4° C. A white precipitate formed and was filtered and washed with distilled water until it was free from acid. The color of the product slowly changed from colorless to light pink or to light brown during filtration.

The vinyl 3HF produced was purified by washing with alcohol followed by recrystallization from dry THF. Yield of the product isolated after the first purification was 13.5 gms (50%).

EXAMPLE 2

4'-styryl-3-hydroxyflavone a) 4-trimethyltin styrene. Grignard reagent was added to a flask containing 18 ml of trimethyltin chloride in 250 ml of THF at $-78°$ C. The reaction mixture was stirred at $-78°$ C. for 3 hrs and RT overnight under nitrogen atmosphere. The reaction mixture was poured into 300 ml of dil. HCl and followed by extraction by 2 portions of 200 ml of solvent ether. The ether layer was dried over anhydrous $MgSO_4$ and filtered. The ether was then evaporated under reduced pressure. A light yellow viscous liquid was obtained, poured into pentane and kept in a freezer overnight. A white precipitate was produced, which was filtered off. Pentane was evaporated under reduced pressure. A light yellow viscous liquid was obtained and was dried under vacuum overnight. A yield of 68% was obtained.

b) 4'-vinyl, 4-biphenyl aldehyde. 1.4 gms (0.075 moles) of 4-bromobenzaldehyde was mixed with 400 mg of $Pd(PPh_3)_4$ catalyst in dry box under an argon atmosphere. 50 ml of ethylene glycol dimethyl ether was added under nitrogen atmosphere and refluxed for 1 hr. In a separate flask, a solution of 2.25 gms (0.15 moles) of styrene trimethyl tin was prepared in 20 ml of ethylene glycol dimethyl ether and flushed with nitrogen for 25 minutes. This was dropwise added to the reaction flask containing bromobenzaldehyde and $Pd(PPh_3)_4$ catalyst. This was followed by the addition of 2 ml of saturated $NaHCO_3$. The reaction mixture was warmed to 60° C. for 48 hrs, after which the reaction was quenched by pouring the reaction mixture into 300 ml of water. 4'-vinyl, 4-biphenyl aldehyde was extracted with three 200 ml extracts of solvent ether. The ether layer was dried over $MgSO_4$ and filtered. Ether was evaporated under reduced pressure. A dark yellow precipitate was obtained and was washed with 200 ml of pentane. A dark yellow residue left after washing with pentane was discarded. The pentane solution was concentrated and 4'-vinyl, 4-biphenyl aldehyde was isolated by recrystallization at low temperature. A white precipitate was obtained, which was filtered and dried under vacuum overnight.

c) 4'styryl, 3-hydroxyflavone. 180 mg of 4'-vinyl, 4-biphenyl aldehyde was mixed with 0.3 ml of 2-hydroxyacetophenone in 30 ml of ethanol. In a separate flask, 2.0 gms of NaOH was dissolved in 10 ml of aq. ethyl alcohol (50%). An NaOH solution was slowly added to the aldehyde solution. The resulting solution slowly changed its color from green to yellow to dark red. The rest of the reaction was carried out according to the method described in Example 1(b) above, producing 4'styryl, 3-hydroxyflavone.

EXAMPLE 3

4'(4"vinyl)biphenylmethane, 3-hydroxyflavone a) 4-bromomethyl benzaldehyde. 4-bromomethyl benzaldehyde was synthesized in two steps.

(i) Synthesis of 1-(bromo) toluenitrile: 4-toluenitrile (0.1 mole) was added to a flask containing N-bromosuccinamide (0.11 mole) and 500 mg of dibenzoyl peroxide in 200 ml of carbon tetrachloride. The reaction mixture was refluxed under nitrogen overnight. The reaction mixture was filtered and the filtrate was concentrated under reduced pressure. Product was recovered by precipitation in 300 ml of hexane. The product was purified by recrystallization from chloroform. The yield of the product was 60%.

(ii) Synthesis of 4-bromomethyl benzaldehyde: A solution of 0.05 moles of diisobutyl aluminium hydride was dropwise added to a flask containing 0.05 moles of 1-(bromo) toluenitrile in 100 ml of benzene at 0° C. The reaction mixture was stirred overnight under nitrogen atmosphere. The reaction was terminated by pouring the entire reaction mixture into dil.HCl in an icebath. The product was isolated by solvent extraction with solvent ether. The ether layer was dried over anhyd. MgSO₄ and the ether layer was concentrated under reduced pressure. The product was recovered by precipitation in pentane. The product was purified by recrystallization from pentane. The yield of 4-bromomethyl benzaldehyde was 70%.

b) 4′vinyl, 4-aldehyde diphenylmethane. 4-trimethyltin styrene may be combined with 4-bromomethyl benzaldehyde following the procedure set forth in Example 2(b) above to produce 4 vinyl, 4-aldehyde diphenylmethane.

c) 4′(4″vinyl)biphenylmethane, 3-hydroxyflavone. 4′vinyl, 4-aldehyde diphenylmethane may be combined with 2-hydroxyacetophenone according to the procedures set forth in Example 1(b) above to produce 4′(4″vinyl)biphenylmethane, 3-hydroxyflavone.

EXAMPLE 4

Poly(vinyl)-3-hydroxyflavone

Polymerization reactions of vinyl-3-hydroxyflavone were carried out in THF at 55° C. using azobisisobutyronitrile (AIBN) as a radical initiator. 500 mg of 4′vinyl-3-hydroxyflavone monomer was transferred to a polymerization tube containing 25 mg of AIBN. 5 ml of dry THF was then added. Monomer was partially soluble in THF at this stage. The polymerization tube was then sealed under high vacuum ($10^{-4}$ torr) after repeated freeze-thaw-pump cycles. Monomer was fully soluble in THF at 55° C. Polymerization was carried out for 72 hrs. The reaction was then stopped by breaking the seal and pouring the contents into ethyl alcohol. A yellow precipitate was obtained and was filtered and washed several times with hot ethyl alcohol. Polymer was purified by dissolving it in THF and precipitating it in ethyl alcohol twice. A 300 mg (approximately 60%) yield of poly(vinyl)-3-hydroxyflavone was obtained.

EXAMPLE 5

Poly(vinyl)-3-hydroxyflavone/polystyrene copolymer

Copolymers containing different weight percentages of 4′vinyl-3-hydroxyflavone were synthesized using AIBN as a radical initiator. Copolymers were prepared having 0.1, 1.0 and 10% by weight infeed of 4′vinyl-3HF. In a typical procedure, 500 mg of 4′vinyl-3HF was mixed with 5 ml of styrene and 5 ml of THF containing 10 mg of AIBN in a polymerization tube. Monomer was partially soluble in THF at this stage. The polymerization tube was then sealed under high vacuum ($10^{-4}$ torr) after repeated freeze-thaw-pump cycles. The monomer was fully soluble in THF once it was warmed to a polymerization temperature of 60° C. When the desired conversion (less than 20%) was reached, the polymerization reaction was stopped by breaking the seal and pouring the contents into ethyl alcohol. A yellow precipitate (poly(vinyl)-3-hydroxyflavone/polystyrene copolymer) was obtained and was filtered and washed several times with hot ethyl alcohol. The copolymer was purified by dissolving it in THF and precipitating it in hot ethyl alcohol twice. Finally the copolymer was filtered and dried in vacuo for 24 hrs. Yield of the copolymer was approximately 1 gm (less than 20%).

EXAMPLE 6

The scintillating properties of poly(4-vinyl)-3HF were demonstated by placing a film of the material in a 3 MeV electron beam. The film of poly(4-vinyl)-3HF was observed to scintillate brightly.

A determination of the absorption and emission behavior of vinyl 3HF monomer and polymer was made in comparison with 3HF using a spectrometer and a fluorimeter. The results of these tests are reported in Table 1.

TABLE 1

| Absorption maximum, nm | | Emission Maximum, nm |
| --- | --- | --- |
| 3HF | 345 | 528 |
| 4-vinyl 3HF | 355 | 541 |
| poly(4-vinyl 3HF) | 350 | 536 |

The tests conducted on 3HF, vinyl 3HF and polyvinyl 3HF indicate that the absorbtion coefficient of vinyl 3HF and polyvinyl 3HF is about twice that of 3HF. The scintillating properties of these materials were demonstrated to be similar.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. An intrinsically scintillating polymer having a repeating unit in the polymer chain derived from a chromophore of the formula:

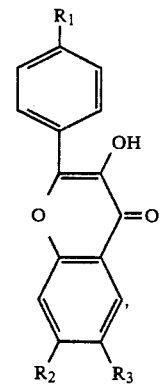

wherein $R_1$ is vinyl, α-methyl vinyl, vinyl phenyl, or vinyl benzyl, and $R_2$ and $R_3$ are independently hydrogen, alkyl, aryl, cyano, nitro, halo, or ether.

2. A polymer as set forth in claim 1 wherein $R_1$ is vinyl or α-methyl vinyl.

3. A polymer as set forth in claim 2 wherein $R_2$ and $R_3$ are hydrogen.

4. A polymer as set forth in claim 1 wherein $R_1$ is vinyl phenyl.

5. A polymer as set forth in claim 4 wherein $R_2$ and $R_3$ are hydrogen.

6. A polymer as set forth in claim 1 wherein $R_1$ is vinyl benzyl.

7. A polymer as set forth in claim 6 wherein $R_2$ and $R_3$ are hydrogen.

8. A polymer as set forth in claim 1 further comprising at least one other repeating unit in the polymer chain.

9. A polymer as set forth in claim 8 wherein said at least one other repeating unit is selected from the group consisting of styrene, vinyl toluene and methyl methacrylate.

10. A polymer as set forth in claim 1 further comprising a styrene repeating unit in the polymer chain.

11. A polymer containing covalently-bonded, low self-absorbing, scintillating chromophores.

* * * * *

UNITED STATES PATENT AND TRADEMARK OFFICE
CERTIFICATE OF CORRECTION

PATENT NO. : 5,258,478
DATED : November 2, 1993
INVENTOR(S) : Joseph B. Schlenoff, Jayesh Dharia, and Kurtis F. Johnson It is certified that error appears in the above-identified patent and that said Letters Patent is hereby corrected as shown below:

In the Abstract, the chemical formula

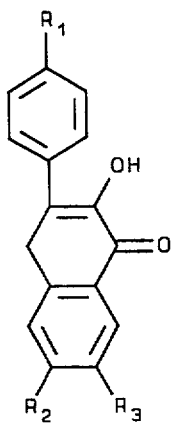

should read

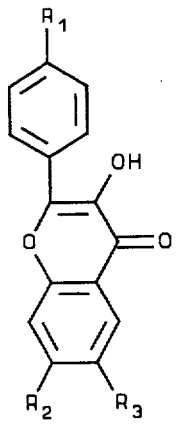

UNITED STATES PATENT AND TRADEMARK OFFICE
CERTIFICATE OF CORRECTION

PATENT NO. : 5,258,478

DATED : November 2, 1993

INVENTOR(S) : Joseph B. Schlenoff, Jayesh Dharia, and Kurtis F. Johnson

It is certified that error appears in the above-identified patent and that said Letters Patent is hereby corrected as shown below:

Column 2, line 61, "-methyl" should read ---α-methyl---.

UNITED STATES PATENT AND TRADEMARK OFFICE
CERTIFICATE OF CORRECTION

PATENT NO. : 5,258,478

DATED : November 2, 1993

INVENTOR(S) : Joseph B. Schlenoff, Jayesh Dharia, and Kurtis F. Johnson

It is certified that error appears in the above-identified patent and that said Letters Patent is hereby corrected as shown below:

Column 9, lines 1-23, formula 11

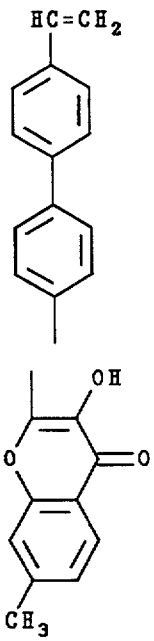

UNITED STATES PATENT AND TRADEMARK OFFICE
CERTIFICATE OF CORRECTION

PATENT NO. : 5,258,478
DATED : November 2, 1993
INVENTOR(S) : Joseph B. Schlenoff, Jayesh Dharia, and Kurtis F. Johnson It is certified that error appears in the above-identified patent and that said Letters Patent is hereby corrected as shown below:

should read

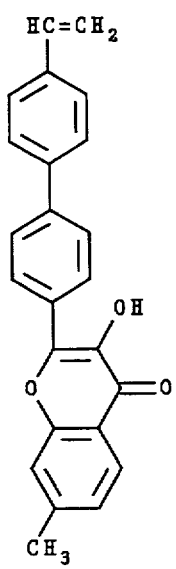

Column 9, lines 24-32, formula 12

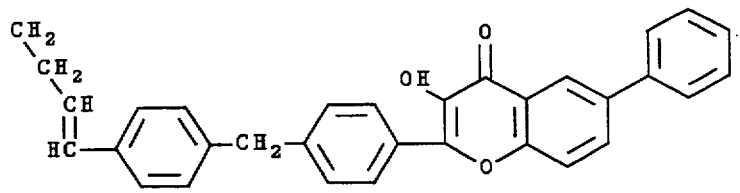

UNITED STATES PATENT AND TRADEMARK OFFICE
CERTIFICATE OF CORRECTION

PATENT NO. : 5,258,478

DATED : November 2, 1993

INVENTOR(S) : Joseph B. Schlenoff, Jayesh Dharia, and Kurtis F. Johnson

It is certified that error appears in the above-identified patent and that said Letters Patent is hereby corrected as shown below:

should read

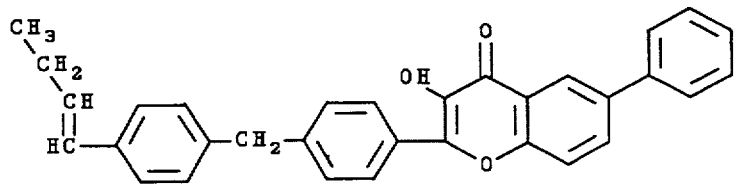

UNITED STATES PATENT AND TRADEMARK OFFICE
CERTIFICATE OF CORRECTION

PATENT NO. : 5,258,478

DATED : November 2, 1993

INVENTOR(S) : Joseph B. Schlenoff, Jayesh Dharia, and Kurtis F. Johnson

It is certified that error appears in the above-identified patent and that said Letters Patent is hereby corrected as shown below:

should read

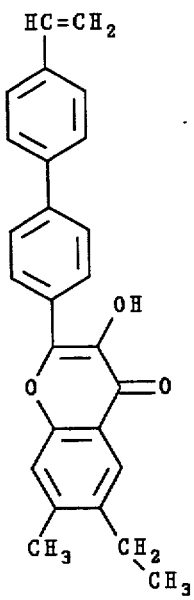

Column 10, line 19 "Produced" should read ---produced---.

UNITED STATES PATENT AND TRADEMARK OFFICE
CERTIFICATE OF CORRECTION

PATENT NO. : 5,258,478

DATED : November 2, 1993

INVENTOR(S) : Joseph B. Schlenoff, Jayesh Dharia, and Kurtis F. Johnson

It is certified that error appears in the above-identified patent and that said Letters Patent is hereby corrected as shown below:

Column 11, line 56, "Precipitate" should read ---precipitate---.

Signed and Sealed this

Twenty-fourth Day of January, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,258,478
DATED        : November 2, 1993
INVENTOR(S)  : Joseph B. Schlenoff, Jayesh Dharia, Kurtis F. Johnson It is certified that error appears in the above-indentified patent and that said Letters Patent is hereby corrected as shown below:

Column 1, line 3, insert the following:

This invention was made with Government support under DOE Grant No. DE-FG05-87ER40319 awarded by the United States Department of Energy. The Government has certain rights in the invention.

Signed and Sealed this

Ninth Day of June, 1998

*Attest:*

BRUCE LEHMAN

*Attesting Officer*  *Commissioner of Patents and Trademarks*